United States Patent [19]

Eikmeier et al.

[11] Patent Number: 5,505,308
[45] Date of Patent: Apr. 9, 1996

[54] SYSTEM FOR THE STORAGE OF TEST ELEMENTS

[75] Inventors: Heino Eikmeier, Lorsch; Klaus-Dieter Sacherer, Kirchheim, both of Germany

[73] Assignee: Boehringer Mannheim GmbH, Mannheim, Germany

[21] Appl. No.: 295,534

[22] Filed: Aug. 25, 1994

[30] Foreign Application Priority Data

Aug. 27, 1993 [DE] Germany ............................ 43 28 815.4

[51] Int. Cl.⁶ ............................ B65D 85/67; B65D 51/04
[52] U.S. Cl. ........................ 206/449; 206/569; 220/264; 220/331
[58] Field of Search ...................... 206/204, 449, 206/455, 456, 804, 44, 569; 220/262–264, 315, 331

[56] References Cited

U.S. PATENT DOCUMENTS

| | | |
|---|---|---|
| 1,458,166 | 6/1923 | Cox . |
| 1,985,615 | 12/1934 | Mitchell .................................. 206/804 |
| 2,562,580 | 7/1951 | Satz et al. ............................... 222/505 |
| 4,464,552 | 8/1984 | Pawlowski .............................. 206/569 |
| 4,681,218 | 7/1987 | Williams ................................ 206/204 |
| 4,834,234 | 5/1989 | Sacherer et al. ....................... 206/204 |
| 4,865,988 | 9/1989 | Guala ..................................... 206/569 |

FOREIGN PATENT DOCUMENTS

| | | |
|---|---|---|
| 3519296A1 | 1/1986 | Germany . |
| 2263273 | 7/1983 | United Kingdom .................... 220/331 |

OTHER PUBLICATIONS

Database WPI, Section Ch, Week 8711, Derwent Publications Ltd. London, GB.

Primary Examiner—Jimmy G. Foster
Attorney, Agent, or Firm—Nikaido, Marmelstein, Murray & Oram

[57] ABSTRACT

The invention is within the field of packaging and storing of test elements that are usually sensitive towards atmospheric humidity or water vapor. The invention concerns a system for the storage of test elements for the analysis of sample liquids in which two or more test elements are present in a storage container which can be sealed water-vapor tight and contains a desiccant inside.

27 Claims, 3 Drawing Sheets

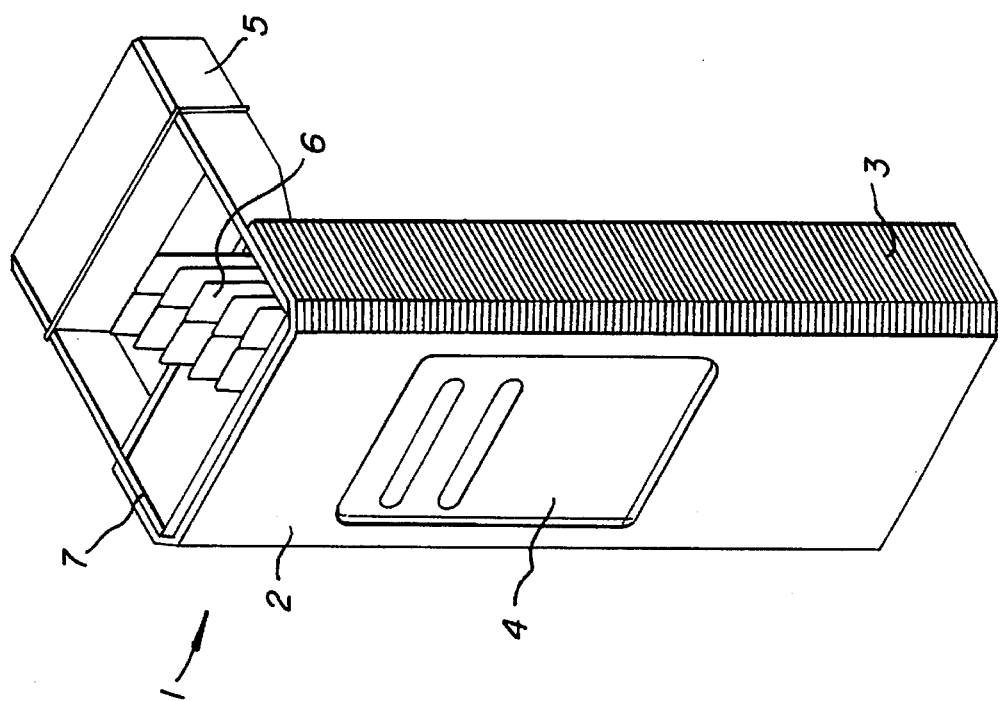
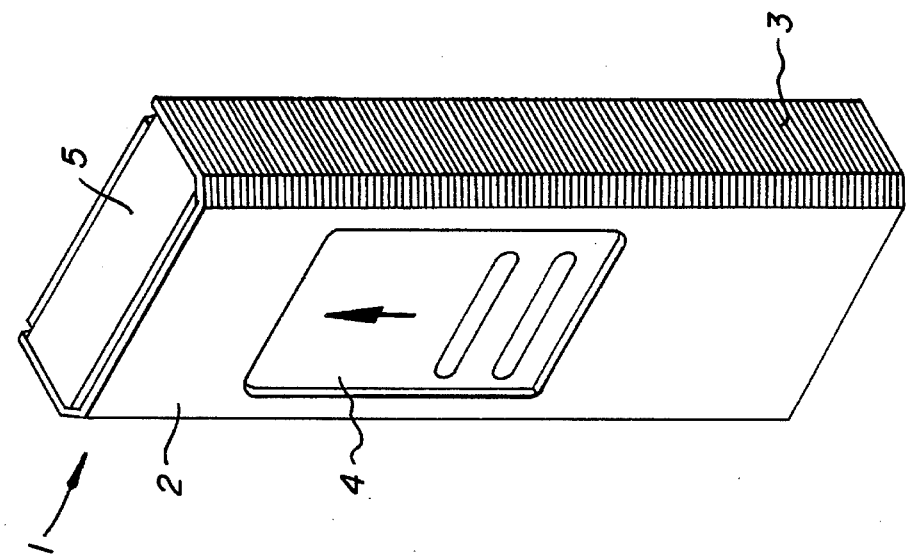

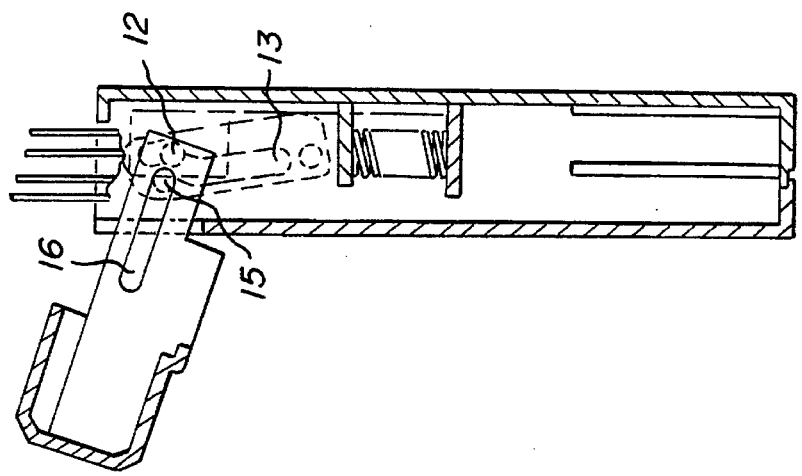
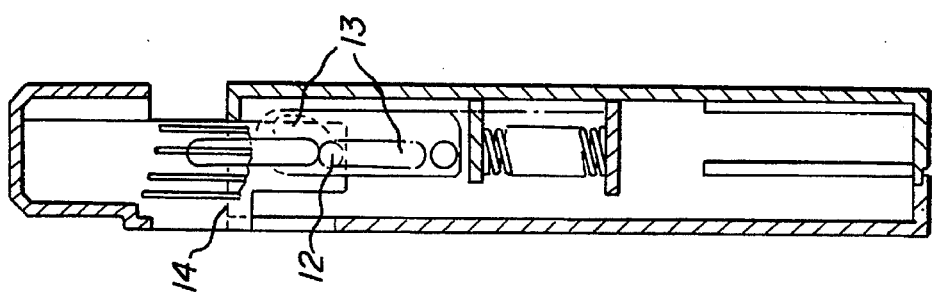
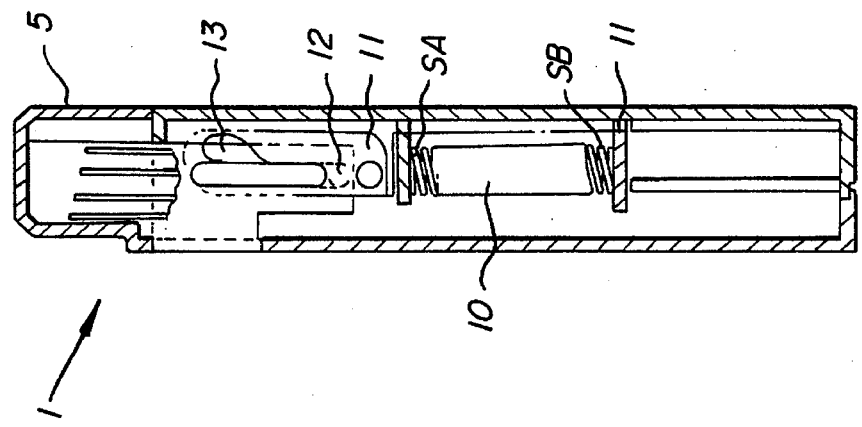

SYSTEM FOR THE STORAGE OF TEST ELEMENTS

The invention concerns a system for the storage of test elements for the analysis of sample liquids in which two or more test elements are present in a storage container which can be closed water-vapour tight and contains a desiccant inside.

The invention is within the field of packaging and storage of test elements which are usually sensitive to air humidity and water vapour.

Storage containers for analytical test elements are known in the state of the art which although providing a water-vapour tight packaging, however, have disadvantages in their handling. For example aluminium tubes are known which are closed with a plastic stopper which carries a desiccant on the side facing the interior of the tube. However, the stopper only seals adequately when it fits securely on the rim of the tube. Stoppers which seal well are therefore difficult to handle and thus uncomfortable for the user. In addition the tube is often left open during the period of sample application which results in moisture reaching the test elements and the desiccant in the stopper becoming loaded with water.

A closure for test element containers is described in a German patent application (DE-35 19296) which has a snap hinge. In order to open or close the vessel, the spring closure is moved over a mechanical resistance. In order that the spring closure makes an adequate seal in the closed state to prevent moisture penetration, the user has to press the spring closure firmly onto the opening until it locks. As in the case of the aluminium tubes, the user must likewise himself take care that the vessel is closed tightly enough after removing test elements.

The object of the invention was therefore to provide a storage system for test elements which ensures an adequate protection of the test elements against air humidity and enables an easy and comfortable handling for the user.

This object is achieved according to the invention by a system for the storage of test elements for the analysis of sample liquids in which two or more test elements are present in the system wherein the system has a flap, a holder, a storage container and a reset device and the flap is pressed either onto the holder or onto the storage container by the reset device so that the test elements inside the system are protected from entry of water vapour.

A system according to the invention serves to store test elements for carrying out analyses without the use of reagent liquids. Usually the said test elements have the form of a strip which leads to an elongated box-type of system. Due to the mechanical devices which are yet to be set forth in detail, boxes with square side faces are preferred.

A system according to the invention comprises a base structure and a flap wherein the base structure can itself comprise a storage container which is present in a holder. The base structure can also be constituted in such a way that it itself serves as a storage container.

In order to enable the user to remove test elements, a system according to the invention has a storage container in which the test elements are inserted in an upright bag from which they can be removed when the system is opened.

The base structure of the system has an opening which is closed by a flap which is pressed or pulled onto the base structure by a spring mechanism. The base structure and flap therefore have a set of surfaces which can lie on top of one another to make a seal when the system is closed. The flap preferably presses onto the opening of the storage vessel and seals the interior of the storage vessel against moisture penetration.

A closure of the interior of the system by the combination of base structure and flap is improved by inserting a readily deformable material, such as foam rubber or a soft plastic, into the rim of the opening of the base structure or to the flap. When the system is closed the deformable material seals the interior of the system against water vapour penetration.

The flap is pressed or pulled onto the opening of the base structure by a spring, a rubber band or other reset devices. When the system is closed, the direction of pull of the reset device is preferably perpendicular to the rim of the opening of the base structure on which the flap rests. The spring mechanism of the reset device is under tension when the system is opened as well as when it is closed.

The system can be opened by the user by pulling the flap away from the base structure against the pull of the reset device. An opened system preferably has no point of rest. A point of rest is only achieved when the system has automatically closed. This inventive property of the system excludes the possibility that the system can remain open without user interaction and that the test elements come into contact with the surrounding air for an extended period.

The protection of the tests contained in the system can be increased further by desiccants in the storage container. Solid desiccants can be used as the desiccant. Silica gels and molecular sieves are preferred.

The flap which closes the system is preferably pulled perpendicularly away from the opening of the base structure and subsequently swung out to the side so that the opening of the base structure is free to facilitate withdrawal of the test elements. It is particularly preferred that the user operates a device such as a slide or lever which opens the flap. This can be achieved by the flap being moved towards the fastening point of the reset device or by the device moving the point of connection between the reset device and base structure. In the latter case the tensile strain of the reset device is reduced whereupon the flap is released from the opening of the base structure.

A system according to the invention can be designed as a non-returnable pack or as a refillable pack i.e. the entire system is either discarded or refilled after removing the test elements. In a preferred, refillable system according to the invention, the base structure takes on the function of a holder for refill packs of test elements. Refill packs are preferably inserted into the base structure from the side opposite to the flap, however, it is also possible according to the invention that the system is opened as when removing test elements and the refill pack is inserted into the base structure through the uncovered opening.

The sealed refill pack must in turn ensure a water-vapour-tight packaging of the test elements before use in the system according to the invention which, however, does not pose any technical problems since a disposable closure can be used. The presence of desiccant in the refill pack increases the stability of the test elements during storage of the refill pack as well as the stability when used in systems according to the invention.

The unsealing and opening of a refill pack for this purpose can be achieved for example by pulling off a band. It can also be unsealed when it is inserted into the base structure of the system e.g. by piercing a seal.

Materials which can serve to construct a system according to the invention are selected in accordance with the requirements for mechanical stability, good machinability and low permeability to water vapour. Metals and plastics come primarily into consideration for the base structure and flap. Whereas metals such as e.g. steel and preferably aluminium intrinsically have a low permeability to water vapour, this requirement is only as a rule achieved for plastics at material thicknesses of over 1 mm. Preferred plastics are polyethylene and polypropylene. Plastics such as foam rubber are preferably used to seal the contact surface of flap and base structure.

The said reset devices can for example be metal or plastic springs or be achieved by elastic bands.

A system according to the invention offers the user the advantage that it is simple and convenient to handle and enables storage of test elements sealed off from atmospheric moisture. An incomplete closing is avoided by the reset mechanism, so that a long stability of the test elements remaining in the system is ensured even when single test elements are removed.

Batch-specific data for the test elements can be mounted alphanumerically, as a bar code or as a magnetic strip on the system i.e. on the base structure or holder, the storage container or the flap. This serves as information for the user about the contents of the storage system. These data can if desired be communicated to an analytical instrument by means of a suitable reading device.

BRIEF DESCRIPTION OF THE DRAWINGS

FIG. 1 is a perspective view of the invention with the flap closed.

FIG. 2 is a perspective view of the invention with the flap opened.

FIG. 3 (A–C) provides cross-section views of the invention in which the flap is closed, partially opened and fully opened.

DESCRIPTION OF THE PREFERRED EMBODIMENT

Figure 5:
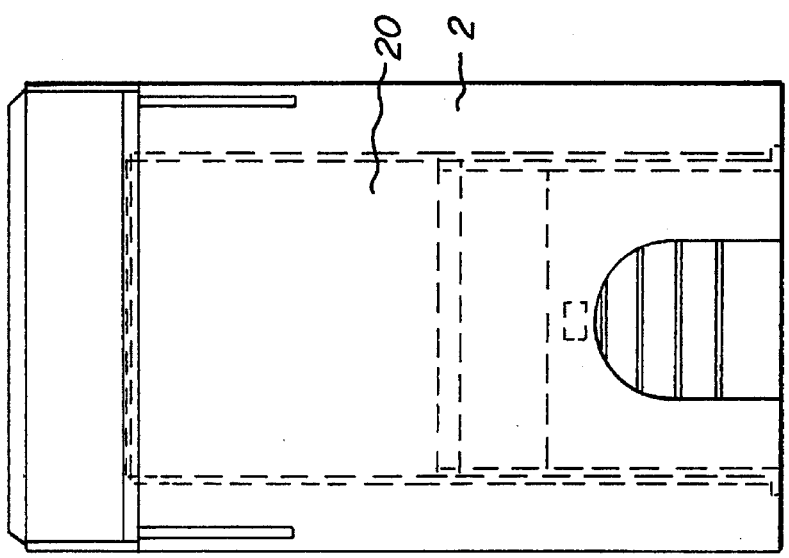
FIG. 5 is a side view of the combination holder and storage container of the invention.

A particularly preferred embodiment of a system according to the invention is illustrated by the following figures:

FIG. 1: closed system

FIG. 2: opened system

FIG. 1: shows a closed system (1) which is in the form of an elongated box. In this embodiment the base structure is composed of a holder (2) and a storage container (20). The holder (2) has corrugations (3) on two opposite sides which serve as holding surfaces. A slide (4) is located on the front side which can be used to open the flap (5). In the closed state the flap (5) matches the surface contour of the base structure.

The system of FIG. 1 is shown in FIG. 2 after the slide (4) has been slid upwards i.e. towards the flap (5). The flap (5) has been pushed out of the holder (2) and folded away to the side so that the test strips (6) are exposed. In order to keep the system open as shown in FIG. 2, the slide (4) must be held in the position shown. If it is released it moves back to the position shown in FIG. 1 and the system closes automatically. It is sealed against water vapour from the surrounding air by the fact that in the closed state the flap (5) presses onto the foam rubber (7) which is located at the opening of the base structure.

The operating mode of the opening mechanism is shown in detail in FIG. 3. FIG. 3A shows a closed system (1). A first side (SA) of the spring (10) is connected to the holder (2) and the second side (SB) is connected to a lever (11). The lever (11) moves a roller (12) which runs in a guide rail (13). The roller (12) is connected mechanically with the flap (5). When the slide is operated, the spring (10) is pressed together as shown in FIG. 3B and the roller (12) moves from the lower end of the guide rail (13) to a middle position. This operation lifts the flap (5) from the opening (14) of the system. FIG. 3C shows which movement the flap (5) makes when the spring (10) is pressed further together. The roller (12) moves to the upper end of the guide rail (13) and the flap (5) swings around an axis defined by a second roller (15). The second roller (15) is mechanically connected to the guide rail (13) and moves within a second guide rail (16) which is located in the flap (5).

Figure 4B:
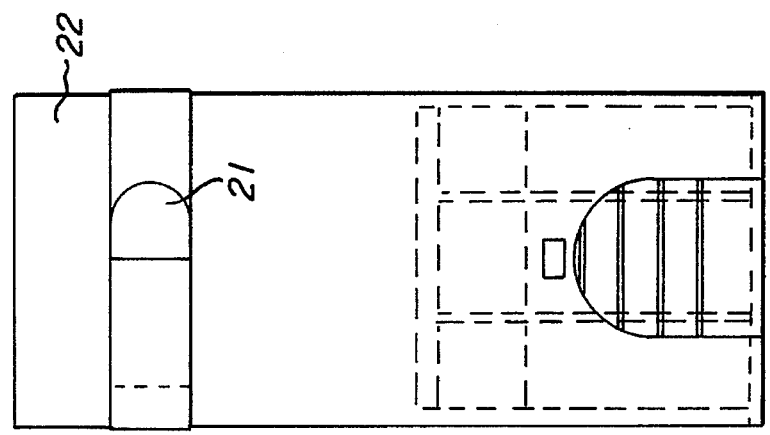
FIG. 4B is a side view of the storage container of FIG. 4A.
Figure 4A:
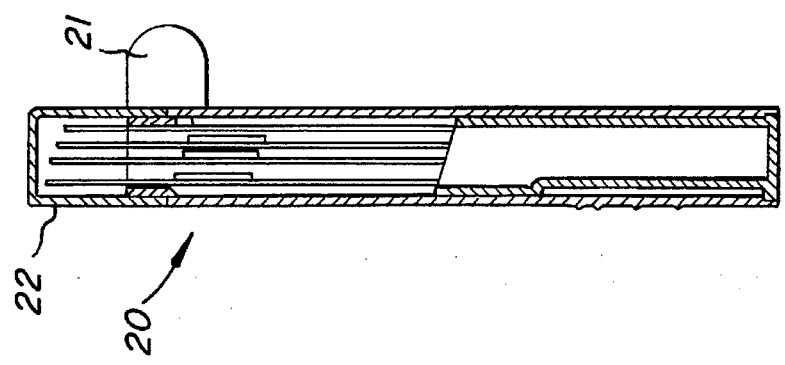
FIGS. 4A is a cross-section view of the closed storage container of the invention.

FIGS. 4A and 4B show a side view of a storage container (20). The storage container (20) is a sealed refill pack in this case. The refill pack has a tearaway flap (21) which is torn off whereupon the closure (22) of the refill pack can be removed.

FIG. 5 shows how the storage container (20) is located within the base structure (2).

LIST OF REFERENCE SYMBOLS (1): system
(2): holder
(3): corrugations
(4): slide
(5): flap
(6): test strip
(7): foam rubber
(10): spring
(11): lever
(12): roller
(13): guide rail
(14): opening
(15): second roller
(16): second guide rail
(20): storage container
(21): tear-away flap
(22): closure
(SA): first side
(SB): second side

We claim:

1. A system for the storage of a plurality of test elements within the system, the test elements being for the analysis of sample liquids, the system comprising
    a holder having an opening;
    a storage container having an opening, for containing the plurality of test elements, and received at least partially within the holder;
    a flap located on one end of the holder, and a reset device; wherein the flap is pressed by the reset device onto the holder opening or the storage container opening to protect test elements inside of the system against water vapor.

2. A system for the storage of a plurality of test elements within the system, the test elements being for the analysis of sample liquids, the system comprising
    a base structure having an opening, and containing the plurality of test elements therein such that the test elements can be removed from the base structure through the opening,
    a flap located on one end of the base structure and releasably closing the opening, and a reset device which moves the flap to open and close the opening and which presses the flap onto the opening to seal the test elements inside of the system against ambient water vapor.

3. System of claim 2, wherein the base structure is a unitary or one-piece unit.

4. System of claim 2, wherein the reset device is located within the base structure.

5. System of claim 2, wherein the base structure comprises a holder having an opening; a storage container having an opening, containing the plurality of test elements, and received at least partially within the holder; and the flap seals one of the openings.

6. System of claim 5, wherein the storage container is removable from the holder.

7. System of claim 6, wherein the storage container can be inserted into the holder from a side opposite the flap.

8. System of claim 2, wherein a desiccant is present inside the base structure.

9. System of claim 2, wherein the base structure has a slide which is operably connected to the flap to open the flap.

10. System of claim 2, wherein a sealing element is located between the flap and the storage container.

11. System of claim 2, wherein batch-specific data of the test elements are located on the system alphanumerically, as bar codes or as magnetic strips.

12. System of claim 2, wherein the system when full contains 10 to 40 test elements.

13. System of claim 2, wherein the reset device automatically closes the opening by pressing on the flap.

14. System of claim 2, wherein the reset device has only one point of rest, and that point of rest is achieved when the flap closes the opening.

15. System of claim 14, wherein the reset device can be digitally engaged by a user to open the flap from the opening, and, upon digital disengagement, the flap automatically returns to a sealing position to seal the opening.

16. A system as claimed in claim 2, wherein said base structure contains test elements which are inserted in a position facing the opening of the system, from which they can be removed when the flap is opened.

17. A system as claimed in claim 2, wherein when said system is closed, said flap is pulled or pressed onto the opening of said base structure by said reset device, and the reset device is under tension at all times.

18. A system as claimed in claim 17, wherein the direction of the press of said reset device is substantially perpendicular to the rim of the opening of said base structure when said system is closed.

19. A system as claimed in claims 1 or 2, wherein said reset device comprises at least one spring.

20. A system for the storage of a plurality of test elements within the system, the test elements being for the analysis of sample liquids, the system comprising storage means having an opening said storage means for containing a plurality of test elements;

holder means for holding the storage means, the holder means having an opening;

flap means located on one end of the holder means, the flap means for sealing one of the openings against passage of water vapor; and reset means for pressing the flap onto said one of the openings to seal same.

21. System of claim 20, wherein the reset means is for digital engagement by a user to move the flap from sealing contact with the opening to permit withdrawal of a test element, and for causing the flap to return to sealing contact with the opening upon digital disengagement.

22. A method for the storage and individual removal of a plurality of test elements for the analysis of sample liquids within a system in which the system is sealed against ambient water vapor, said method comprising moving a flap sealing an opening of a base structure away from the opening, removing at least one test element from a storage compartment located within said base structure, and urging said flap against the opening of said base structure by automatically engaging a reset device which has only one point of rest in the system, that point of rest being achieved when said flap closes said opening to cause said flap to automatically return to a sealing position to seal the opening.

23. A method as claimed in claim 22, the method further comprising operating an opening device which moves said flap away from the opening of said base structure.

24. A method as claimed in claim 23, the method further comprising moving a point of connection between said reset device and said base structure.

25. A method as claimed in claim 22, the method further comprising initially forcing said flap perpendicularly away from the opening of said base structure by said reset device when said system is opened.

26. A method as claimed in claim 25, the method further comprising forcing said flap towards the side of said base structure device upon further opening so that the test elements can be withdrawn from the opening of said base structure.

27. Method of claim 22, wherein the flap is moved away from the opening by digital engagement of the reset device by a user, and the flap automatically is returned to the sealing position upon digital disengagement.

* * * * *